Figure 1:
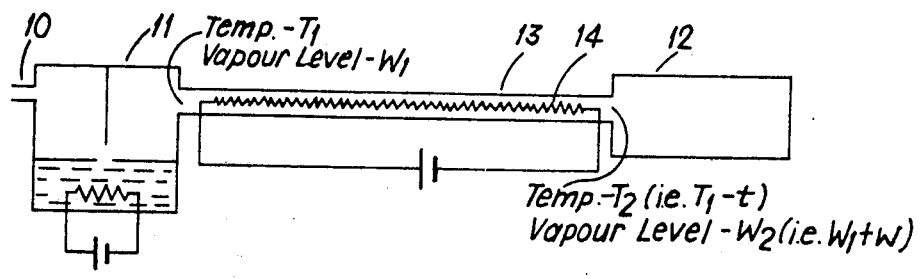

United States Patent [19]
Grant

[11] 4,060,576
[45] Nov. 29, 1977

[54] METHOD AND APPARATUS FOR VAPOR SATURATED GAS DELIVERY

[76] Inventor: Graham Cameron Grant, 205 Wigram Road, Glebe, N.S.W. 2037, Australia

[21] Appl. No.: 611,382

[22] Filed: Sept. 8, 1975

Related U.S. Application Data

[63] Continuation of Ser. No. 396,032, Sept. 10, 1973, abandoned.

[30] Foreign Application Priority Data

Sept. 13, 1972 Australia .................................. 0427
Nov. 17, 1972 Australia .................................. 1267

[51] Int. Cl.² ............... A61M 15/00; B01F 15/06
[52] U.S. Cl. ................... 261/130; 128/192; 219/272; 219/275; 219/276; 219/362; 261/70; 261/119 R; 261/142; 261/153; 261/DIG. 65
[58] Field of Search ......... 261/142, 152, 153, 119 R, 261/70, 130, DIG. 65; 128/192, 186–188, 193, 194; 219/271–273, 275, 276, 362; 239/133, 134, 136

[56] References Cited

U.S. PATENT DOCUMENTS

| 1,323,181 | 11/1919 | Goodfellow | 128/192 |
|---|---|---|---|
| 2,585,132 | 2/1952 | Kalmadge | 261/119 R X |
| 3,178,159 | 4/1965 | Johnson | 261/142 X |
| 3,434,471 | 3/1969 | Liston | 128/192 X |
| 3,638,926 | 2/1972 | Melville et al. | 261/142 X |
| 3,659,604 | 5/1972 | Melville et al. | 219/276 X |
| 3,695,516 | 10/1972 | Rogers | 219/362 X |
| 3,721,802 | 3/1973 | Chrisman | 219/275 X |
| 3,799,517 | 3/1974 | Tamm | 261/142 X |

FOREIGN PATENT DOCUMENTS

| 523,252 | 10/1928 | Germany | 261/142 |
|---|---|---|---|
| 576,213 | 3/1932 | Germany | 261/142 |

*Primary Examiner*—Tim R. Miles
*Assistant Examiner*—Richard L. Chiesa
*Attorney, Agent, or Firm*—Ladas, Parry, Von Gehr, Goldsmith & Deschamps

[57] ABSTRACT

A method of controlling the delivery-point temperature and vapor level of a gas which is conveyed through a delivery line from a heater/humidifier to a delivery point. The method is particularly applicable to apparatus for use in the medical field and it involves heating and humidifying the gas to a temperature $T_1$ and to a vapor level $W_1$ of less than 100% saturation, and controlling the temperature of the gas in the delivery line to provide for a lower temperature $T_2$ which corresponds to a selected higher vapor level $W_2$ at the delivery point.

7 Claims, 4 Drawing Figures

U.S. Patent  Nov. 29, 1977  4,060,576
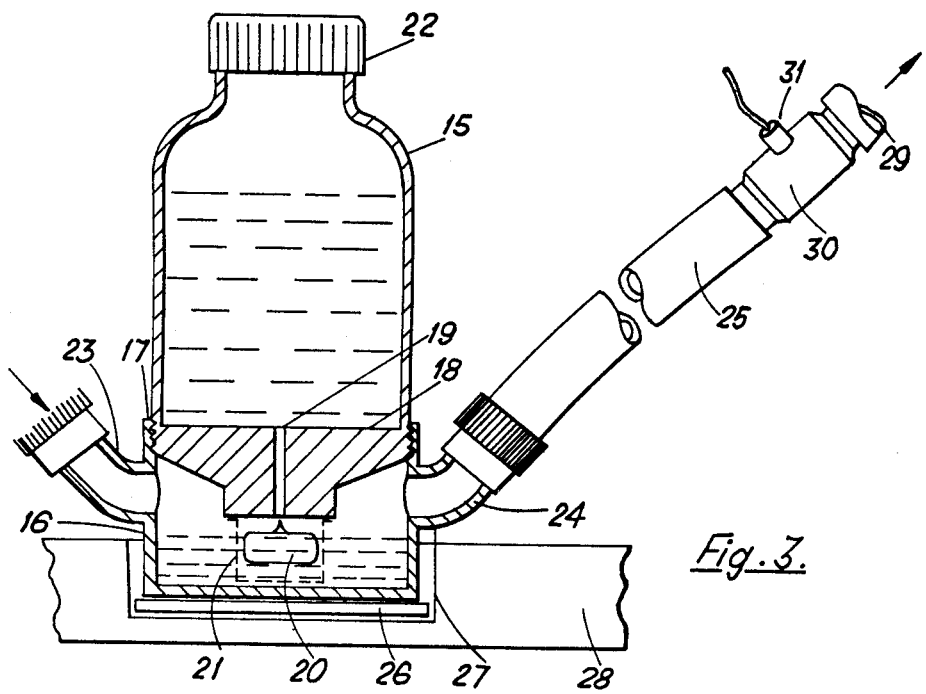
_Fig. 3._
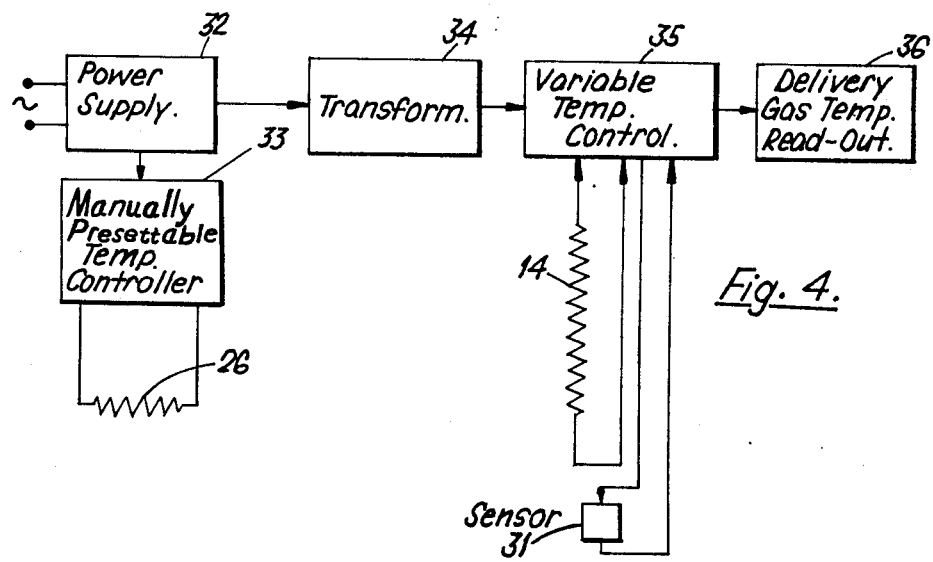
_Fig. 4._

METHOD AND APPARATUS FOR VAPOR SATURATED GAS DELIVERY

CROSS REFERENCE TO RELATED APPLICATION

This is a continuation application of Ser. No. 396,032, filed Sept. 10, 1973, now abandoned.

This invention relates to the delivery of temperature and vapour level controlled gases to a delivery point.

The invention has particular, but non-exclusive, application in relation to humidifiers for use in the medical field and it is herein described for convenience of reference in this context.

When a normal person breathes atmospheric air his air passages supply heat and moisture to the inhaled gases, the body being capable of supplying the required amount of heat and moisture. However under certain conditions in medical practice a patient's mechanism of supplying heat and moisture is interfered with, and it becomes necessary to provide an artificial means for warming inspired gases to a point at or near normal body temperature (37° C) before the gas is delivered to the patient. Similarly, it is necessary to humidify the inspired gases to a level at or near full (100%) saturation.

Temperature and vapour level controlled air might typically be required to be delivered to a shocked or very ill patient, to a patient whose air passages have been bypassed by a tube or tracheotomy for artificial ventilation, to a neonatal patient (who has a low reserve of heat and moisture) undergoing intensive care, or to a patient who is subject to prolonged breathing of cylinder stored compressed gases.

Apparatus which is currently employed for the conditioning of gases to be delivered to a patient generally takes the form of either a so-called nebuliser or a heated humidifier. Nebulisers function to produce fine water droplets in a heated gas suspension, by a process of atomisation but they are noisy in operation and they are prone to failure as a result of atomiser jet blockage. Heated humidifiers function by supplying heat and moisture to a gas by the passage of the gas through or over a heated waterbath or evaporative surface.

The heated humidifier type apparatus is currently manufactured in one or other of two forms (vis., a simple humidifier or a heated hose humidifier), but each has its characteristic disadvantages. In the simple humidifier gases are passed over heated water within a tank and to a patient by way of a flexible hose. Considerable heat losses to atmosphere occur during passage of the gas through the hose and, in order to obtain a delivery temperature at or near body temperature, it is necessary to heat the tank water to a very much higher temperature. This results in heavy condensation along the hose length and, unless the condensate is cleared from the system a potentially hazardous situation could be created.

In the (known) heated hose humidifiers the delivery hose is itself heated in order that gases delivered from the humidifying tank are maintained at a constant temperature, and in order to avert condensation within the hose. However, in such apparatus the humidifier itself has been run at or near normal body temperature and (because a simple tank humidifier will not produce vapour at above approximately 80% saturation at the gas flows involved) a much larger than normal evaporative surface is required. This has involved a complicated apparatus which is difficult to service and clean.

The present invention seeks to avoid the problems associated with known gas conditioning apparatus by providing a novel method of delivering gas to a delivery point; the method comprising heating and humidifying the gas to a temperature $T_1$ and to a vapour level $W_1$ of less than 100% saturation, and transferring the gas to a delivery point via a delivery line, the temperature of the gas in the delivery line being controlled to provide for a lower temperature $T_2$ (i.e., $T_1 - t$) which corresponds with a selected high vapour level $W_2$ (i.e., $W_1 + w$) at the delivery point.

The invention as above defined contrasts with the prior art methods which, in their more sophisticated form, traditionally involve saturating the gas, at the generation stage to meet delivery point vapour level requirements and maintaining a temperature along the delivery line which results in preservation of the desired vapour level. Thus, whereas the prior art techniques require saturation level control of the gas in the delivery line, the present invention resides in the concept of obtaining a desired vapour level at the delivery point only.

The invention has particular application in the delivery of air or oxygen to a patient and, in such case, the vapour level of the gas would normally be controlled to provide for fully or near-fully saturated vapour at the delivery point. The temperature control of the gas in the delivery line might be effected by way of a water-jacket type heat exchanger or by way of heating element (e.g., an electrical resistance type heating element) located within or about the delivery line.

The invention may also be defined as providing a gas conditioning apparatus comprising a humidifier incorporating means for heating and humidifying a gas to a temperature $T_1$ and a vapour level $W_1$ of less than 100% saturation, a delivery line connected with the humidifier and for delivering the gas to a delivery point, and a secondary heater associated with the delivery line and which controls the temperature of the gas passing therethrough to provide for a lower temperature $T_2$ which corresponds with a selected higher vapour level $W_2$ at the delivery point.

In a preferred form of the invention a temperature control sensing element is located in the gas stream at the delivery end of the line, and the heat applied to the gas passing through the delivery line is regulated to provide for the desired delivery point temperature.

This permits the use of a simple type of humidifier and the high, initial, heating of the gas. Thus, the humidifier does not itself need to produce full saturation this being achieved by allowing for a temperature drop along the line.

It is acknowledged that a simple type of humidifier might give varying degrees of saturation with changes in gas flow through the system, assuming that the delivery point temperature is maintained constant. However any such variation would be regarded as unimportant in practice because, provided the gases are delivered to a patient at or near full saturation, the actual value is not considered to be critical.

Figure 2:
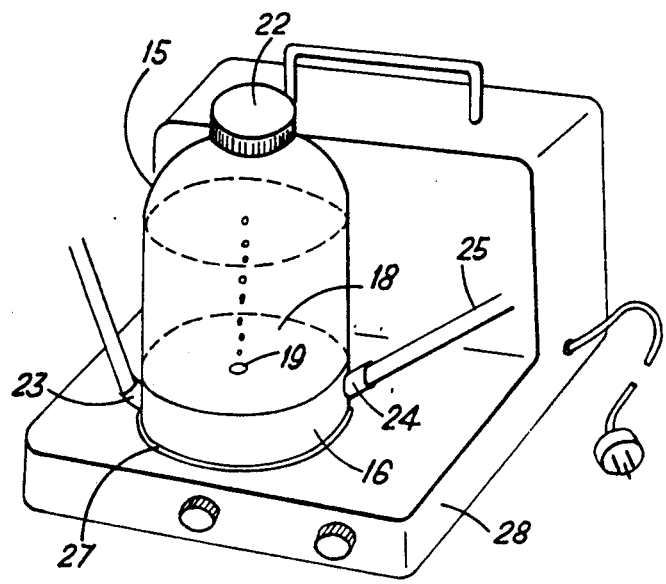

The invention will be more fully understood from the following description of a preferred embodiment thereof taken in conjunction with the accompanying drawings wherein, FIG. 1 is a schematic representation of the broad principle of the invention, FIG. 2 is a perspective view of a humidifying apparatus for use in medical applications and which embodies the invention, FIG. 3 is an elevation view of a portion of the humidifying apparatus, and FIG. 4 is a schematic representation of electrical circuitry associated with the apparatus.

As shown in FIG. 1, a gas such as air or oxygen is delivered by way of a conduit 10 to a heated tank type humidifier 11, at which the vapour level of the gas is raised to a desired level, and the gas is passed from the humidifier to a delivery point 12, typically a patient, via a flexible delivery line 13.

The humidifier 11 is controlled to provide for vapour saturation of the gas to a level $W_1$ less than 100% R.H. and, typically, to a level of 80–90% saturation. Also, the humidifier provides for heating the vapour to a temperature $T_1$ which is higher than a temperature $T_2$ required of the gas upon its delivery to the patient.

Then, to provide for delivery of the gas to the patient at a (desired) higher vapour level $W_2$, typically at full saturation, the temperature along the delivery line is controlled to give the lower temperature $T_2$ at the delivery point. Temperature control is effected in order to offset losses along the delivery line by locating a resistance heater 14 within the line.

The above described method of controlling the temperature vapour level of a gas is utilised in the humidifying apparatus shown in FIGS. 2 to 4 of the drawings. However, before proceeding with a description of the illustrated apparatus it is noted that, in the interest of convenience and economics, a single humidifier should be suitable for both adult and paediatrics use, and to meet this requirement the following criteria must be satisfied:

a. For adults, the surface area of evaporation must be large enough to provide for high level saturation at large gas flows, and the capacity of the water reservoir must be sufficiently large to avoid the need for constant refilling; and, b. For infants, the compression volume of the reservoir should be as small as possible so as to reduce the compliance of the circuit as much as possible.

A simple humidifying tank cannot be used to meet these two seemingly conflicting requirements at the same time and it has been appreciated by the inventor that it is necessary to have a water reservoir separated from an evaporating chamber, and to maintain a constant water level within the evaporating chamber by feeding the chamber with water from the reservoirs when required. The evaporation chamber can then be kept quite small, in the interest of preserving a low compression volume. However, if there is direct communication between the reservoir and the evaporating chamber nothing will be gained, because the air within the reservoir might still be compressed.

The inventor has overcome this problem by providing a valve which closes during the compression (inspiratory) phase but which operates to let water pass from the reservoir as required during the expiratory phase.

Thus, as shown in FIGS. 2 and 3, the apparatus comprises a reservoir 15 which is mounted to an evaporating chamber 16, the two portions 15 and 16 being screw connected at 17.

The lower end of the reservoir is formed with a base 18, and the reservoir communicates with the evaporating chamber 16 by way of a port 19. A desired water level is maintained within the evaporating chamber by a float supported needle valve 20 which is located within a cage portion 21 of the reservoir base.

The float 20 serves to maintain an optimum level in the evaporating chamber and to seal against the port 19 when the water level in the chamber 16 rises and when there is gas compression in the chamber, during an inspiratory phase.

An air-tight cap 22 closes the reservoir, so that if the float 20 should fail the water level in the evaporating chamber will be prevented from rising above the level of the lower end of the port and thereby obstruct the respiratory circuit. Also, a fail-safe high/low water sensor device (not shown) is incorporated in the wall of the evaporating chamber 16.

Air (or oxygen) to be heated and humidified is directed into the chamber 16 by way of an inlet port 23, and the heated-humidified air passes from the chamber by way of an exit port 24 and delivery line 25.

Heat transfer to the water within the chamber 16 and to air passing through the chamber is effected by way of a heating coil 26 upon which the evaporating chamber normally sits. The heating coil is located within a pocket portion 27 of a casing 28 which serves to house control gear associated with the humidifier. The control gear is hereinafter described with reference to FIG. 4 of the drawings.

The delivery line 25 is constituted by a flexible plastic hose which has a helical form electrical resistance element (14 see FIG. 1) embedded in its wall, and the resistance element functions as a secondary heater, as above described with reference to FIG. 1. Also, the delivery line 25 is connected to, for example, an endotracheal tube connector 29 by way of a coupling 30.

The coupling 30 is fitted within its interior with a sensor 31, such as a thermister or platinum resistance element, which is wired to the control gear. The sensor serves to detect the temperature level of gas passing from the delivery line and the control regulation of electrical energy, applied to the resistance element 14.

The control gear associated with the above described apparatus is shown in FIG. 4 and it includes a power supply 32 (which may be a main supply). The power supply is connected through a manually pre-settable temperature controller 33 to the air/water heater 26, and through a transformer 34 to a variable temperature controller 35. The temperature controller 35 provides low voltage energising current to the heater coil 14, the current level being selectively variable to effect a required heat transfer to gas passing through the delivery line 25. Adjustment of the controller 35 (to provide for current variation) is effected both manually and automatically, the automatic adjustment being controlled by the sensor 31.

A delivery gas temperature read-out device 36, which is controlled by the sensor 31, is incorporated in the circuit.

In operation of the device above described, the heater 14 is controlled manually and/or automatically (as above mentioned) to provide for a desired gas temperature $T_2$ at the delivery end of the line 25. Also, the heating level of the heater coil 26 is adjusted and set to effect heating of the gas passing through the evaporating chamber 16 to a temperature $T_1$ which will provide for a desired humidity level $W_2$ at the delivery point temperature $T_2$.

Therefore, although the simple type of humidifier described herein would not normally produce full saturation of a gas within the evaporating chamber at flow rates which would be required, this is not a problem. The temperature of the system in accordance with the above described embodiment may be adjusted in such a manner that a controlled temperature drop (i.e., $T_1 - T_2$) is permitted along the delivery line to produce full saturation at the delivery point. By controlling the temperature drop in such a manner that full saturation does not occur before the delivery point, condensation is prevented from occurring within the delivery line.

A further significant feature of the device above described is that the reservoir cap 22 may be removed to permit replenishment of the reservoir 15 without there being a need to disconnect the device from a patient circuit.

I claim:

1. Gas conditioning apparatus, comprising:
    a gas humidifier including means defining a water evaporation chamber in said humidifier;
    first heating means for heating water in said evaporation chamber;
    a presettable temperature controller for controlling said first heating means to control the water temperature in said chamber;
    a gas delivery line extending between said gas humidifier and a delivery point;
    a second heater associated with and extending along substantially the entire length of said delivery line;
    a temperature sensor detecting the temperature of gas leaving the delivery line; and,
    a variable temperature controller responsive to said temperature sensor and controlling the secondary heater to alter the heat applied thereby to gas flowing through said line,
    said first heating means heating said gas in said humidifier to a temperature $T_1$ and a vapour level $W_1$ of significantly less than 100% saturation and the variable temperature controller operating independently to maintain the gas temperature at the delivery point at a second temperature $T_2$, lower than $T_1$, with a selected vapour level $W_2$ which is higher than $W_1$.

2. A gas conditioning apparatus as claimed in claim 10 wherein the sensing element is connected in circuit with means adapted to provide a read-out of gas temperature at the delivery end of the delivery line.

3. A gas conditioning apparatus as claimed in claim 1 wherein the humidifier comprises a reservoir, a removable cap closing said reservoir in air-tight manner, an evaporation chamber communicating with the reservoir by way of a water feed port having a top end in the reservoir and a bottom end in the evaporation chamber, gas inlet and outlet ports communicating with the evaporation chamber about the level of the water feed port bottom end, and a valve which functions to admit the water to the evaporation chamber from the reservoir but to prevent water within the evaporation chamber from reaching such level that it interferes with gas passage between the inlet and outlet ports or flows out through them should the valve stick in the open condition.

4. A gas conditioning apparatus as claimed in claim 1 wherein valve means within the evaporation chamber controls the flow of water thereto and wherein the valve means is operated to a closed position when gas compression is effected within the evaporation chamber.

5. A gas conditioning apparatus as claimed in claim 1 wherein heat is transferred to the evaporating chamber by variable temperature heating element.

6. Apparatus for humidifying and heating gas to be breathed by a patient undergoing anaesthesia, artificial respiration, or the like, comprising:
    a humidification tank;
    a primary heater heating a humidifying liquid in said humidification tank and raising said gas to a temperature above normal body temperature and humidifying said gas to a predetermined humidity of up to 85% while passing through said tank;
    a primary temperature sensing element located in said humidification tank, said primary temperature sensing element detecting the temperature of gas or liquid in said humidification tank;
    a delivery line connected with the humidification tank for delivering gas to a delivery point;
    a secondary heater associated with and extending along substantially the entire length of said delivery line for heating humidified gas passing therethrough;
    a secondary sensing element located in the delivery point end portion of said delivery line and adapted to detect the temperature of gas passing from said delivery line; and
    a control circuit (a) controlling the heat supplied to said humidification tank by said primary heater in accordance with the temperature detected by said primary temperature sensing element and maintaining said gas or liquid at a temperature above normal body temperature by an amount determined in accordance with the humidity level of gas passing from said humidification tank, and (b) controlling the heat supplied to the secondary heating element in accordance with the temperature detected by said secondary sensing element so that said gas passes from said delivery line at about 100% relative humidity and about normal body temperature.

7. A method for humidifying and heating gas to be breathed by a patient undergoing anaesthesia, artificial respiration, or the like, comprising:
    passing said gas into a humidification tank containing humidifying liquid;
    heating the humidifying liquid in said humidification tank thereby heating said gas in the humidification tank to a temperature above a temperature at which it is to be breathed by the patient and humidifying said gas to a humidity of up to 85% with vapor from the humidifying liquid in said tank;
    transferring said gas from said humidification tank to a delivery point via a heated delivery line;
    sensing the temperature of gas passing from said delivery line; and
    controlling automatically the amount of heat supplied to said gas in said delivery line in accordance with the temperature of gas passing from said delivery line so that said gas passes from said delivery line at about normal body temperature and about 100% relative humidity.

* * * * *